(12) United States Patent  
Feder et al.

(10) Patent No.: US 7,374,892 B2
(45) Date of Patent: May 20, 2008

(54) METHODS AND COMPOSITIONS FOR DIAGNOSIS AND TREATMENT OF IRON OVERLOAD DISEASES AND IRON DEFICIENCY DISEASES

(75) Inventors: John N. Feder, San Carlos, CA (US); Pamela J. Bjorkman, Pasadena, CA (US); Randall C. Schatzman, Daly City, CA (US)

(73) Assignees: Bio-Rad Laboratories, Inc., Hercules, CA (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 11/501,582

(22) Filed: Aug. 8, 2006

(65) Prior Publication Data

US 2006/0287236 A1  Dec. 21, 2006

Related U.S. Application Data

(60) Continuation of application No. 10/092,404, filed on Mar. 4, 2002, now Pat. No. 7,119,170, which is a division of application No. 09/094,964, filed on Jun. 12, 1998, now Pat. No. 6,391,852, which is a continuation-in-part of application No. 08/876,010, filed on Jun. 13, 1997, now abandoned.

(51) Int. Cl.
G01N 33/53 (2006.01)
A61K 38/00 (2006.01)

(52) U.S. Cl. .......................................... 435/7.1; 514/2
(58) Field of Classification Search ..................... None
See application file for complete search history.

(56) References Cited

U.S. PATENT DOCUMENTS

| 4,399,216 | A | 8/1983 | Axel et al. |
|---|---|---|---|
| 4,434,156 | A | 2/1984 | Trowbridge |
| 4,511,503 | A | 4/1985 | Olson et al. |
| 4,666,927 | A | 5/1987 | Hider et al. |
| 4,683,202 | A | 7/1987 | Mullis |
| 4,711,845 | A | 12/1987 | Gelfand et al. |
| 4,912,118 | A | 3/1990 | Hider et al. |
| 5,075,469 | A | 12/1991 | Chevion |
| 5,104,865 | A | 4/1992 | Hider et al. |
| 5,116,964 | A | 5/1992 | Capon |
| 5,185,368 | A | 2/1993 | Peter et al. |
| 5,256,676 | A | 10/1993 | Hider et al. |
| 5,328,992 | A | 7/1994 | Peter et al. |
| 5,385,918 | A | 1/1995 | Connell et al. |
| 5,399,346 | A | 3/1995 | Anderson et al. |
| 5,420,008 | A | 5/1995 | Nishida et al. |
| 5,424,057 | A | 6/1995 | Peter et al. |
| 5,582,979 | A | 12/1996 | Weber |
| 5,705,343 | A | 1/1998 | Drayna et al. |
| 5,712,098 | A | 1/1998 | Tsuchihashi et al. |
| 5,719,125 | A | 2/1998 | Suzuki et al. |
| 5,753,438 | A | 5/1998 | Drayna et al. |
| 5,872,237 | A | 2/1999 | Feder et al. |
| 6,025,130 | A | 2/2000 | Thomas et al. |
| 6,140,305 | A | 10/2000 | Thomas et al. |
| 6,228,594 | B1 | 5/2001 | Thomas et al. |
| 6,284,732 | B1 | 9/2001 | Feder et al. |
| 6,391,852 | B1 | 5/2002 | Feder et al. |
| 2005/0090430 | A1 | 4/2005 | Feder et al. |

FOREIGN PATENT DOCUMENTS

| CA | 2115221 | 8/1994 |
|---|---|---|
| CA | 2115222 | 8/1994 |
| CA | 2115224 | 8/1994 |
| DE | 208 609 | 4/1984 |
| DE | 4 327 226 | 2/1995 |
| EP | 0 315 434 | 5/1989 |
| EP | 0 346 281 | 12/1989 |
| EP | 97910741 | 6/2003 |
| GB | 2 293 269 | 3/1996 |
| WO | WO 94/01463 | 1/1994 |
| WO | WO 94/04186 | 3/1994 |
| WO | WO 94/11367 | 5/1994 |
| WO | WO 94/21243 | 9/1994 |
| WO | WO 95/16663 | 6/1995 |
| WO | WO 96/06583 | 3/1996 |
| WO | WO 96/17870 | 6/1996 |
| WO | WO 96/35802 | 11/1996 |
| WO | WO 97/38137 | 10/1997 |
| WO | WO97/38137 | 10/1997 |
| WO | WO98/65814 | 12/1998 |

OTHER PUBLICATIONS

Adams, M.D., et al., "Complementary DNA Sequencing: Expressed Sequence Tags and Human Genome Project," Science (1991) 252:1651-1656 (National Institutes of Health).
Ahmed, R and Stevens JG. Viral Persistence.. In Fundamental Virology, Second Edition, Fields, et al., eds. Raven Press, Ltd., New York. p. 252, 1991.
Amadou, C., et al., "Localization of New Genes and Markers to the Distal Part of the Human Major Histocompatibility Complex (MHC) Region and Comparison With the Mouse: New Insights Into the Evolution of Mammalian Genomes," Genomics (1995) 26:9-20 (0888-7543/95).
Anderson et al., 1990, "Transferrin receptor distribution and regulation in the rat small intestine. Effect of iron stores and erythropoiesis," *Gastroenterology*, 98(3):576-585.
Anderson, J.R., et al., "Precipitating Autoantibodies in Sjögren's Disease," Lancet (1961) 2:456-460 (Glasgow Univ.).
Bacon, B.R., "Causes of Iron Overload," N. Engl. J. Med. (1992) 326(2):126-127 (St. Louis Univ. School of Medicine).
Balan, V., et al., "Screening for Hemochromatosis: A Cost-Effectiveness Study Based on 12,258 Patients," Gastroenterology (1994) 107:453-459 (0016-5085/94).

(Continued)

*Primary Examiner*—David A. Saunders
*Assistant Examiner*—F. Pierre VanderVegt
(74) *Attorney, Agent, or Firm*—Jones Day

(57) ABSTRACT

Methods and compositions are provided for the diagnosis and treatment of iron overload diseases and iron deficiency diseases.

1 Claim, 5 Drawing Sheets

OTHER PUBLICATIONS

Barton, J.C., et al., "*Blood Lead Concentrations in Hereditary Hemochromatosis,*" J. Lab. Clin. Med. (1994) 124(2):193-198 (0022-2143/94).

Barton, J.C., et al., "*Hemochromatosis: The Genetic Disorder of the Twenty-First Century,*" Nature Medicine (1996) 2(4):394-395 (Brookwood Medical Center).

Beaucage, S.L., et al., "*Deoxynucleoside Phosphoramidites—A New Class of Key Intermediates for Deoxypolynucleotide Synthesis,*" Tetrahedron Letters (1981) 22(20):1859-1862 (0040-4039/81).

Beggs, J.D., "*Transformation of Yeast by a Replicating Hybrid Plasmid,*" Nature (1978) 275:104-109 (0028-0836/78).

Benton, W.D., et al., "*Screening λgt Recombinant Clones by Hybridization to Single Plaques in situ,*" Science (1977) 196:180-182 (National Institutes of Health).

Beutler, E. et al., "Mutation Analysis in Hereditary Hemochromatosis" Blood Cells, Molecules, and Diseases (1996), 22(16): 187-194.

Beutler, E., et al., "*A Strategy for Cloning the Hereditary Hemochromatosis Gene,*" Blood Cells, Molecules, and Diseases (1995) 21(21):207-216 (1079-9796/95).

Boretto, J., et al., "*Anonymous Markers Located on Chromosome 6 in the HLA-A Class I Region: Allelic Distribution in Genetic Haemochromatosis,*" Hum. Genet. (1992) 89:33-36 (Institut National de la Sante et de la Recherche Medicale).

Botstein, D., et al., "*Sterile Host Yeasts (SHY): A Eukaryotic System of Biological Containment for Recombinant DNA Experiments,*" Gene (1979) 8:17-24 (American Cancer Society).

Broach, J.R., et al., "*Transformation in Yeast: Development of a Hybrid Cloning Vector and Isolation of the CAN1 Gene,*" Gene (1979) 8:121-133 (National Institutes of Health).

Calandro, L.M., et al., "*Characterization of a Recombinant That Locates the Hereditary Hemochromatosis Gene Telomeric to HLA-F,*" Hum. Genet. (1995) 96:339-342 (Kaiser Foundation Research Institute).

Camaschella, C., et al., "*Hereditary Hemochromatosis: Recent Advances in Molecular Genetics and Clinical Management,*" Haematologica (1997) 82:77-84 (BioMed).

Campbell, A.M., "*Monoclonal Antibody Technology,*" Elsevier Science Publishers (1985) Chapter 1 pp. 1-32 (ISBN 0-444-80592-3).

Capecchi, M.R., "*Altering the Genome by Homologous Recombination,*" Science (1989) 244:1288-1292 (Univ. of Utah Medical Center).

Cartwright, G.E., et al., "*Inheritance of Hemochromatosis: Linkage to HLA,*" Trans. Assoc. Am. Phys. (1978) 91:273-281 (National Institutes of Health).

Chen, X., et al., "*Template-Directed Dye-Terminator Incorporation (TDI) Assay: A Homogeneous DNA Diagnostic Method Based on Fluorescence Resonance Energy Transfer,*" Nucl. Acids Res. (1997) 25(2):347-353 (U.S. Dept. of Energy).

Chong, S.S., et al., "*Molecular Cloning of the cDNA Encoding a Human Renal Sodium Phosphate Transport Protein and its Assignment to Chromosome 6p21.3-p23,*" Genomics (1993) 18:355-359 (0888-7543/93).

Church, D.M., et al., "*Isolation of Genes From Complex Sources of Mammalian Genomic DNA Using Exon Amplification,*" Nature Genetics (1994) 6:98-105 (National Institutes of Health).

Clark, G., et al., "*Characterization of a Soluble Cytoplasmic Antigen Reactive With Sera From Patients With Systemic Lupus Erythmatosus,*" J. Immunol. (1969) 102(1):117-122 (Univ. of New York Dept. of Medicine ).

Cornall, R.J., et al., "*The Generation of a Library of PCR-Analyzed Microsatellite Variants for Genetic Mapping of the Mouse Genome,*" Genomics (1991) 10:874-881 (0888-7543/91).

Crawford, D.H.G., et al., "*Evidence That the Ancestral Haplotype in Australian Hemochromatosis Patients May be Associated With a Common Mutation in the Gene,*" Am. J. Hum. Genet. (1995) 57:362-367 (0002-9297/95).

Crystal, R.G., "*Gene Therapy Strategies for Pulmonary Disease,*" Am. J. Med. (1992) 92(6A):6A-44S-6A-52S (National Institutes of Health).

Darnell, J., "*Tools of Molecular Cell Biology: Molecular Technology,*" Scientific American Books (1986) pp. 227-229 (Rockefeller Univ.).

Dausset, J., et al., "*Centre d'Etude du Polymorphisme Humain (CEPH): Collaborative Genetic Mapping of the Human Genome,*" Genomics (1990) 6:575-577 (0888-7543/90).

de Sousa, M., et al., "*Iron Overload in $\beta_2$-Microglobulin-Deficient Mice,*" Immun. Lett. (1994) 39:105-111 (0165-2478/94).

Dugast, I.J., et al., "*Identification of Two Human Ferritin H Genes on the Short Arm of Chromosome 6,*" Genomics (1990) 6:204-211 (0888-7543/90).

Edwards, C.Q., et al., "*Screening of Hemochromatosis,*" New Engl. J. Med. (1993) 328(22):1616-1619 (Univ. of Utah College of Medicine).

Edwards, C.Q., et al., "*The Locus for Hereditary Hemochromatosis Maps Between HLA-A and HLA-B,*" Cytogenet. Cell Genet. (1985) 40:620 (Univ. of Utah Medical Center).

El Kahloun, A., et al., "*Localization of Seven New Genes Around the HLA-A Locus,*" Hum. Molec. Genet. (1992) 2(1):55-60 (Institut National de la Sante et de la Recherche Medicale).

Fahy, E., et al., "*Self-Sustained Sequence Replication (3SR): An Isothermal Transcription-Based Amplification System Alternative to PCR,*" PCR Methods and Applications (1991) 1:25-33 (1054-9803/91).

Finch, C.A., "*Hemochromatosis—Treatment is Easy, Diagnosis Hard,*" Western J. Med. (1990) 153(3):323-325 (Univ. of Washington School of Medicine).

Freemont, P.S., et al., "*A Novel Cysteine-Rich Sequence Motif,*" Cell (1991) 65:483-484 (Imperial Cancer Research Fund).

Friedmann, T., "*Progress Toward Human Gene Therapy,*" Science (1989) 244:1275-1281 (San Diego Univ. of Calif.).

Fullan, A., et al., "*A Polymorphic Dinucleotide Repeat at the Human HLA-F Locus,*" Hum. Mol. Genet. (1994) 3(12):2266 (Mercator Genetics).

Gandon et al., "Linkage Disequilibrium and Extended Haplotypes in the HLA-A to D6S105 Region: Implications for Mapping the Hemochromatosis Gene (HFE)," J. Hum. Genet. (1996) 97 (1):103-13.

Gasparini, et al, "Where does the gene for Hemochromatosis lie in relation to HLA-A", Hepatology (1994), 19: 1050-1056.

Gasparini, P., et al., "*Linkage Analysis of 6p21 Polymorphic Markers and the Hereditary Hemochromatosis: Localization of the Gene Centromeric to HLA-F,*" Hum. Molec. Genet. (1993) 2(5):571-576 (National Research Council).

Gnirke, A., et al., "*Physical Calibration of Yeast Artificial Chromosome Contig Maps by RecA-Assisted Restriction Endonuclease (RARE) Cleavage,*" Genomics (1994) 24:199-210 (0888-7543/94).

Goei, V.L., et al., "*Isolation of Novel Non-HLA Gene Fragments From the Hemochromatosis Region (6p21.3) by cDNA Hybridization Selection,*" Am. J. Hum. Genet. (1994) 54:244-251 (0002-9297/94).

Gorski, J., "*HLA-DR β-Chain Polymorphism: Second Domain Polymorphism Reflects Evolutionary Relatedness of Alleles and May Explain Public Serologic Epitopes,*" J. Immunol. (1989) 143(1):329-333 (0022-1767/89).

Gruen, J.R., et al., "*Physical and Genetic Mapping of the Telomeric Major Histocompatibility Complex Region in Man and Relevance to the Primary Hemochromatosis Gene (HFE),*" Genomics (1992) 14:232-240 (0378-7543/92).

Grunstein, M., et al., "*Colony Hybridization: A Method for the Isolation of Cloned DNAs That Contain a Specific Gene,*" Proc. Natl. Acad. Sci. USA (1975) 72(10):3961-3965 (National Science Foundation).

Gubler, U., et al., "*A Simple and Very Efficient Method for Generating cDNA Libraries,*" Gene (1983) 25:263-269 (0888-1119/83).

Gyapay, G., et al., "*The 1993-1994 Genethon Human Genetic Linkage Map,*" Nature Genetics (1994) 7:246-339 (Assoc. Francais conte les Myopathies).

Halliday, J.W., "*Hemochromatosis and Iron Needs,*" Nutr. Rev. (1998) 56(2):S30-S37 (Queensland Institute of Medical Research).

Harlow, E., et al., "*Antibodies: A Laboratory Manual,*" Cold Spring Harbor Laboratory (1988) Chapter 5 pp. 75-81 (ISBN 0-87969-314-2).

Harrison et al., 2003, *J. of Hepatology*, vol. 38: S14-S23.

Hashimoto, K., et al. "Identification of a Mouse Homolog for the Human Hereditary Haemochromatosis Candidate Gene," Biochem. Biophys. Res. Comm. (1997) 230:35-39 (0006-291X/97).

Hemochromatosis-Genetics Home Reference. http://ghr.nlm.nih.giv/condition+Hemochromatosis.

Herskowitz, I., et al., "The Lysis-Lysogeny Decision of Phage λ: Explicit Programming and Responsiveness," Ann. Rev. Genet. (1980) 14:399-455 (0066-4197/80).

Hinnen, A., et al., "Transformation of Yeast," Proc. Natl. Acad. Sci. USA (1978) 75(4):1929-1933 (National Science Foundation).

Ito, H., et al., "Transformation of Intact Yeast Cells Treated With Alkali Cations," J. Bacteriol. (1983) 153(1):163-168 (0021-9193/83).

Jack, L.J.W., et al., "Cloning and Analysis of cDNA Encoding Bovine Butyrophilin, an Apical Glycoprotein Expressed in Mammary Tissue and Secreted in Association With the Milk-fat Globule Membrane During Lactation," J. Biol. Chem. (1990) 265(24):14481-14486 (National Science Foundation).

Jakobovits, A., et al., "Production of Antigen-Specific Human Antibodies from Mice Engineered with Human Heavy and Light Chain YACs$^a$", Ann. N.Y. Acad. Sci. (1995) 764:525-535 (Cell Genesys, Inc.).

Jazwinska, E.C., et al., "Haplotype Analysis in Australian Hemochromatosis Patients: Evidence for a Predominant Ancestral Haplotype Exclusively Associated with Hemochromatosis," Am. J. Hum. Genet. (1995) 56:428-433 (0002-9297/95).

Jazwinska, E.C., et al., "Hemochromatosis and "HLA-H": Definite!," Hepatology (1997) 25(2):495-496 (Queensland Institute of Medical Research).

Jazwinska, E.C., et al., "Localization of the Hemochromatosis Gene Close to D6S105," Am. J. Hum. Genet. (1993) 53:347-352 (0002-9297/93).

Jazwinska, E.C.,et al., "Where Does the Gene for Hemochromatosis Lie in Relation to HLA-A?," Hepatology (1994) 19:1050-1051 (Queensland Institute of Medical Research).

Jouet, M.M.H., et al., "Isolation of YAC Clones Containing Class I HLA Genes Which Map in the Vicinity of the Hereditary Haemochromatosis Gene," J. Med. Genet. (1991) 28(8):572 (St. Mary's Hospital, Manchester).

Koller, B.H., et al., "Normal Development of Mice Deficient in $\beta_2M$, MHC Class I Proteins, and $CD8^+T$ Cells," Science (1990) 248:1227-1230 (National Institutes of Health).

Kramer, M.F., et al., "The Polymerase Chain Reaction," Current Protocols in Molecular Biology (1993) Chapter 15 pp. 15.0.1-15.1.14 (ISBN 0-471-30661-4).

Lemarchand, P., et al., "Adenovirus-Mediated Transfer of a Recombinant Human $\alpha_1$-Antitrypsin cDNA to Human Endothelial Cells," Proc. Natl. Acad. Sci. USA (1992) 89:6482-6486 (National Institutes of Health).

Levy-Lahad, E., et al., "Candidate Gene for the Chromosome I Familial Alzheimer's Disease Locus," Science (1995) 269:973-977 (National Institute on Aging for the Alzheimer's Disease Research Center).

Lipinski, M., et al., "Idiopathic Hemochromatosis: Linkage with HLA," Tissue Antigens (1978) 11:471-474 (Hopital Saint-Louis, Paris).

Lovett, M., et al., "Direct Selection: A Method for the Isolation of cDNAs Encoded by Large Genomic Regions," Proc. Natl. Acad. Sci. USA (1991) 88:9628-9632 (National Center for Human Genome Research).

Maskos, U., et al., "A Novel Method for the Parallel Analysis of Multiple Mutations in Multiple Samples," Nucl. Acids Res. (1993) 21(9):2269-2270 (Univ. of Oxford).

Matteucci, M.D., et al., "Synthesis of Deoxyoligonucleotides on a Polymer Support," J. Am. Chem. Soc. (1981) 103:3185-3191 (National Institutes of Health).

Maxam, A.M., et al., "Sequencing End-Labeled DNA With Base-Specific Chemical Cleavages," Methods in Enzymology (1980) 65:499-560 (ISBN 0-12-181965-5).

Miller, M.M., et al., "Immunoglobulin Variable-Region-Like Domains of Diverse Sequence Within the Major Histocompatibility Complex of the Chicken," Proc. Natl. Acad. Sci. USA (1991) 88:4377-4381 (National Institutes of Health).

Miyazaki, J.I., et al., "Intracellular Transport Blockade Caused by Disruption of the Disulfide Bridge in the Third External Domain of Major Histocompatibility Complex Class I Antigen," Proc. Natl. Acad. Sci. USA (1986) 83:757-761 (National Institutes of Health).

Morgan, J.G., et al., "The Selective Isolation of Novel cDNAs Encoded by the Regions Surrounding the Human Interleukin 4 and 5 Genes," Nucl. Acids Res. (1992) 20(19):5173-5179 (National Center for Human Genome Research).

Murray, J.C., et al., "A Comprehensive Human Linkage Map with Centimorgan Density," Science (1994) 265:2049-2054 (Univ. of Iowa).

Needham-VanDevanter, D.R., et al., "Characterization of an Adduct Between CC-1065 and a Defined Oligodeoxynucleotide Duplex," Nucl. Acids Res. (1984) 12(15):6159-6168 (Welch Foundation).

Needleman, S.B., et al., "A General Method Applicable to the Search for Similarities in the Amino Acid Sequence of Two Proteins," J. Mol. Biol. (1970) 48:443-453 (U.S. Public Health Service).

Nickerson, D.A., et al., "Genotyping by Ligation Assays," Current Protocols in Human Genetics (1994) Chapter 2.6 pp. 2.6.1-2.6.4 (ISBN 0-471-03420-7).

Nickerson, D.A., et al., "Automated DNA Diagnostics Using an ELISA-Based Oligonucleotide Ligation Assay," Proc. Natl. Acad. Sci. USA (1990) 87:8923-8927 (Whittier Foundation).

Nierman, W.C., et al., "ATCC/NIH Repository Catalogue of Human and Mouse DNA Probes and Libraries," Amer. Type Culture Coll. (1994) pp. 1-70 (ISBN 0-930009-56-8).

Olynyk, J.K., et al., "Hepatic Iron Concentration as a Predictor of Response to Interferon Alfa Therapy in Chronic Hepatitis C," Gastroenterology (1995) 108:1104-1109 (0016-5085/95).

Orphanos, V., et al., "Thirteen Dinucleotide Repeat Polymorphisms on Chromosome 6," Hum. Mol. Genet. (1993) 2(12):2196 (Cancer Genetics).

Orum, H., et al., "Single Base Pair Mutation Analysis by PNA Directed PCR Clamping," Nucl. Acids Res. (1993) 21(23):5332-5336 (Research Center for Medical Biotechnology).

Patterson, M., et al., "Molecular Characterization of Cell Cycle Gene CDC7 From Saccharomyces cerevisiae," Mol. Cell Biol. (1986) 6(5):1590-1598 (0270-7306/86).

Pearson, J.D., et al., "High-Performance Anion-Exchange Chromatography of Oligonucleotides,", J. Chromatog. (1983) 255:137-149 (0021-9673/83).

Pearson, W.R., et al., "Improved Tools for Biological Sequence Comparison," Proc. Natl. Acad. Sci. USA (1988) 85:2444-2448 (National Institutes of Health).

Phatak, P.D., et al., "Cost-Effectiveness of Screening for Hereditary Hemochromatosis," Arch. Intern. Med. (1994) 154:769-776 (Rochester General Hospital, NY).

Queen, C., et al., "Cell-Type Specific Regulation of a κ Immunoglobulin Gene by Promoter and Enhancer Elements," Immunol. Rev. (1986) 89:49-68 (National Institutes of Health).

Raha-Chowdhury, R., et al., "Allelic Associations and Homozygosity at Loci from HLA-B to D6S299 in Genetic Haemochromatosis," J. Med. Genet. (1995) 32:446-452 (Univ. of Wales College of Medicine).

Raha-Chowdhury, R., et al., "New Polymorphic Microsatellite Markers Place the Haemochromatosis Gene Telomeric to D6S105," Hum. Mol. Genet. (1995) 4(10):1869-1874 (Univ. of Wales College Medicine).

Roberts, A.G., et al., "Increased Frequency of the Haemochromatosis Cys282Tyr Mutation in Sporadic Porphyria Cutanea Tarda," Lancet (1997) 349:321-323 (Univ. of Wales College of Medicine).

Roth, M.P., et al., "The Human Myelin Oligodendrocyte Glycoprotein (MOG) Gene: Complete Nucleotide Sequence and Structural Characterization," (1995) Genomics 28:241-250 (0888-7543/95).

Rothenberg, B.E., et al., "The Molecular Mechanisms of Iron Overload: An Animal Model for Hemochromatosis," FASEB J. (1994) 8. Abstract No. 5217, p. A900 (Univ. of California).

Rothenberg, B.E., et al., "β₂ *Knockout Mice Develop Parenchymal Iron Overload: A Putative Role for Class I Genes of the Major Histocompatibility Complex in Iron Metabolism*," Proc. Natl. Acad. Sci. USA (1996) 93:1529-1534 (National Institutes of Health).

Saiki, R.K., et al., "*Primer-Directed Enzymatic Amplification of DNA with a Thermostable DNA Polymerase*," Science (1988) 239:487-491 (Cetus Corp.).

Salter, R.D., "*Intracellular Transport of Class I HLA Molecules is Affected by Polymorphic Residues in the Binding Groove*," Immunogenetics (1994) 39:266-271 (American Cancer Society).

Schild, H., et al., "*The Nature of Major Histocompatiblity Complex Recognition by γδ T Cells*," Cell (1994) 76:29-37 (German Cancer Research Center).

Schneider, I., "*Cell Lines Derived From Late Embryonic Stages of Drosophila Melanogaster*," J. Embryol. Exp. Morph. (1972) 27(2):353-365 (Walter Reed Army Institute of Research).

Seese, et al., "*Localization of the Hemochromatosis Disease Gene: Linkage Disequilibrium Analysis using an American Patient Collection*," Blood Cells, Molecules & Diseases (1996) 22:36-46.

Sevier, E.D., "*Monoclonal Antibodies in Clinical Immunology*," Clin. Chem. (1981) 27(11):1797-1806 (Hybritech, Inc.).

Simon M., et al., "*Association of HLA-A3 and HLA-B14 Antigens With Idiopathic Haemochromatosis*," Gut (1976) 17:332-334 (Hopital Pontchaillou, France).

Simon, M., et al., "*A Study of 609 HLA Haplotypes Marking for the Hemochromatosis Gene*: (1) *Mapping of the Gene Near the HLA-A Locus and Characters Required to Define a Heterozygous Population and* (2) *Hypothesis Concerning the Underlying Cause of Hemochromatosis-HLA Association*," Am. J. Hum. Genet. (1987) 41:89-105 (0002-9297/87).

Smith, T.F., et al., "*Comparison of Biosequences*," Adv. Appl. Math. (1981) 2:482-489 (0196-8858/81).

Sood, A. K., et al., "*Isolation and Partial Nucleotide Sequence of a cDNA Clone for Human Histocompatibility Antigen HLA-B by Use of an Oligodeoxynucleotide Primer*," Proc. Natl. Acad. Sci. USA (1981) 78(1):616-620 (National Institutes of Health).

Sprague, J., et al., "*Expression of a Recombinant DNA Gene Coding for the Vesicular Stomatitis Virus Nucleocapsid Protein*," J. Virol. (1983) 45(2):773-781 (0022-538X/83).

Stone, C., et al., "*Isolation of CA Dinucleotide Repeats Close to D6S105; Linkage Disequilibrium With Haemochromatosis*," Hum. Molec. Genet. (1994) 3(11):2043-2046 (Queensland Institute of Medical Research).

Strathmann, M., et al., "*Transposon-Facilitated DNA Sequencing*," Proc. Natl. Acad. Sci. USA (1991) 88:1247-1250 (U.S. Public Health Service Program).

Summers, K.M., et al., "*Fine Mapping of a Human Chromosome 6 Ferritin Heavy Chain Pseudogene: Relevance to Haemochromatosis*," Hum. Genet. (1991) 88:175-178 (Queensland Institute of Medical Research).

Summers, K.M., et al., "*HLA Determinants in an Australian Population of Hemochromatosis Patients and Their Families*," Am. J. Hum. Genet. (1989) 45:41-48 (0002-9297/89).

Taylor, M.R., et al., "*Cloning and Sequence Analysis of Human Butyrophilin Reveals a Potential Receptor Function*," Biochimica et Biophysica Acta (1996) 1306:1-4 (0167-4781/96).

Thiede, C., et al., "*Simple and Sensitive Detection of Mutations in the Ras Proto-Oncogenes Using PNA-Mediated PCR Clamping*," Nucl. Acids Res. (1996)24(5):983-984 (Wilhelm-Sander Stiftung).

Totaro, A., et al., "*Hereditary Hemochromatosis: Generation of a Transcription Map Within a Refined and Extended Map of the HLA Class I Region*," Genomics (1996) 31:319-326 (0888-7543/96).

Totaro, A., et al., "*New Polymorphisms and Markers in the HLA Class I Region: Relevance to Hereditary Hemochromatosis (HFE)*," Hum. Genet. (1995) 95:429-434 (Italian Ministry of Health).

Vernet, C., et al., "*Evolutionary Study of Multigenic Families Mapping Close to the Human MHC Class I Region*," J. Mol. Evol. (1993) 37:600-612 (National Science Foundation).

Vogel, et al., "*Human Chromosomes*," Springer-Verlag (1992) pp. 18-81.

Wagner, R., et al., "*Mutation Detection Using Immobilized Mismatch Binding Protein (MutS)*," Nucl. Acids Res. (1995) 23(19):3944-3948 (Genecheck Inc.).

Walker, G.T., et al., "*Isothermal in vitro Amplification of DNA by a Restriction Enzyme/DNA Polymerase System*," Proc. Natl. Acad. Sci. USA (1992) 89:392-396 (Becton Dickinson Research Center).

Wallace, R.B., et al., "*Hybridization of Synthetic Oligodeoxyribonucleotides to Φ$_{102}$ 174 DNA: The Effect of Single Base Pair Mismatch*," Nucl. Acids Res. (1979) 6(11):3543-3557 (City of Hope National Medical Center).

Weber, J.L., et al., "*Dinucleotide Repeat Polymorphism at the D6S105 Locus*," Nucl. Acids Res. (1991) 19(4):968 (National Institutes of Health).

Wettstein, D.A., et al., "*Expression of a Class II Major Histocompatibility Complex (MHC) Heterodimer in a Lipid-Linked Form With Enhanced Peptide/Soluble MHC Complex Formation at Low pH*," J. Exp. Med. (1991) 174:219-228 (0022-1007/91).

Worwood, M., et al., "*Alleles at D6S265 and D6S105 Define a Haemochromatosis-Specific Genotype*," Brit. J. Hematol. (1994) 86:863-866 (Univ. of Wales College of Medicine).

Wu, D.Y., et al., "*The Ligation Amplification Reaction (LAR)-Amplification of Specific DNA Sequences Using Sequential Rounds of Template-Dependent Ligation*," Genomics (1989) 4:560-569 (0888-7543/89).

Yanofsky, C., et al., "*Repression is Relieved Before Attenuation in the trp Operon of Escherichia coli as Tryptophan Starvation Becomes Increasingly Severe*," J. Bacter. (1994) 158(3):1018-1024 (0021-9193/84).

Youil, R., et al., "*Screening for Mutations by Enzyme Mismatch Cleavage With T4 Endonuclease VII*," Proc. Natl. Acad. Sci. USA (1995) 92:87-91 (National Health and Medical Research Council of Australia).

Yu, C-E., et al., "*Positional Cloning of the Werner's Syndrome Gene*," Science (1996) 272:258-262 (National Institute on Aging).

Zijlstra, M., et al., "*β2-Microglobulin Deficient Mice Lack CD4⁻8⁺Cytolytic T Cells*," Nature (1990) 344:742-746 (Cancer Research Institute).

Zinkernagel, R.M., et al., "*MHC-Restricted Cytotoxic T Cells: Studies on the Biological Role of Polymorphic Major Transplantation Antigens Determining T-Cell Restriction-Specificity, Function, and Responsiveness*," Adv. In Immunol. (1979) 27:51-177 (ISBN 0-12-022427-5).

IP: Anti-HFE
Blot: Anti-TfR

IP: Anti-HFE
Blot: Anti-FLAG(M2)

IP: Anti-TfR
Blot: Anti-HFE

IP: Anti-TfR
Blot: Anti-TfR

IP: Anti-FLAG(M2)
Blot: Anti-TfR

```
                            SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 276 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Arg Leu Leu Arg Ser His Ser Leu His Tyr Leu Phe Met Gly Ala Ser
     1               5                  10                  15

Glu Gln Asp Leu Gly Leu Ser Leu Phe Glu Ala Leu Gly Tyr Val Asp
                    20                  25                  30

Asp Gln Leu Phe Val Phe Tyr Asp His Glu Ser Arg Arg Val Glu Pro
                35                  40                  45

Arg Thr Pro Trp Val Ser Ser Arg Ile Ser Ser Gln Met Trp Leu Gln
            50                  55                  60

Leu Ser Gln Ser Leu Lys Gly Trp Asp His Met Phe Thr Val Asp Phe
     65                 70                  75                  80

Trp Thr Ile Met Glu Asn His Asn His Ser Lys Glu Ser His Thr Leu
                    85                  90                  95

Gln Val Ile Leu Gly Cys Glu Met Gln Glu Asp Asn Ser Thr Glu Gly
                   100                 105                 110

Tyr Trp Lys Tyr Gly Tyr Asp Gly Gln Asp His Leu Glu Phe Cys Pro
               115                 120                 125
```

```
Asp Thr Leu Asp Trp Arg Ala Ala Glu Pro Arg Ala Trp Pro Thr Lys
    130                 135                 140

Leu Glu Trp Glu Arg His Lys Ile Arg Ala Arg Gln Asn Arg Ala Tyr
145                 150                 155                 160

Leu Glu Arg Asp Cys Pro Ala Gln Leu Gln Gln Leu Leu Glu Leu Gly
                165                 170                 175

Arg Gly Val Leu Asp Gln Gln Val Pro Pro Leu Val Lys Val Thr His
                180                 185                 190

His Val Thr Ser Ser Val Thr Thr Leu Arg Cys Arg Ala Leu Asn Tyr
                195                 200                 205

Tyr Pro Gln Asn Ile Thr Met Lys Trp Leu Lys Asp Lys Gln Pro Met
    210                 215                 220

Asp Ala Lys Glu Phe Glu Pro Lys Asp Val Leu Pro Asn Gly Asp Gly
225                 230                 235                 240

Thr Tyr Gln Gly Trp Ile Thr Leu Ala Val Pro Pro Gly Glu Glu Gln
                245                 250                 255

Arg Tyr Thr Cys Gln Val Glu His Pro Gly Leu Asp Gln Pro Leu Ile
                260                 265                 270

Val Ile Trp Glu
        275

(2) INFORMATION FOR SEQ ID NO: 2:

(i) SEQUENCE CHARACTERISTICS:
        (A) LENGTH: 276 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Arg Leu Leu Arg Ser His Ser Leu His Tyr Leu Phe Met Gly Ala Ser
1               5                   10                  15

Glu Gln Asp Leu Gly Leu Ser Leu Phe Glu Ala Leu Gly Tyr Val Asp
                20                  25                  30

Asp Gln Leu Phe Val Phe Tyr Asp Asp Glu Ser Arg Arg Val Glu Pro
            35                  40                  45

Arg Thr Pro Trp Val Ser Ser Arg Ile Ser Ser Gln Met Trp Leu Gln
    50                  55                  60

Leu Ser Gln Ser Leu Lys Gly Trp Asp His Met Phe Thr Val Asp Phe
65                  70                  75                  80

Trp Thr Ile Met Glu Asn His Asn His Ser Lys Glu Ser His Thr Leu
                85                  90                  95

Gln Val Ile Leu Gly Cys Glu Met Gln Glu Asp Asn Ser Thr Glu Gly
                100                 105                 110

Tyr Trp Lys Tyr Gly Tyr Asp Gly Gln Asp His Leu Glu Phe Cys Pro
                115                 120                 125

Asp Thr Leu Asp Trp Arg Ala Ala Glu Pro Arg Ala Trp Pro Thr Lys
    130                 135                 140

Leu Glu Trp Glu Arg His Lys Ile Arg Ala Arg Gln Asn Arg Ala Tyr
145                 150                 155                 160

Leu Glu Arg Asp Cys Pro Ala Gln Leu Gln Gln Leu Leu Glu Leu Gly
                165                 170                 175

Arg Gly Val Leu Asp Gln Gln Val Pro Pro Leu Val Lys Val Thr His
                180                 185                 190
```

His Val Thr Ser Ser Val Thr Thr Leu Arg Cys Arg Ala Leu Asn Tyr
            195                 200                 205

Tyr Pro Gln Asn Ile Thr Met Lys Trp Leu Lys Asp Lys Gln Pro Met
    210                 215                 220

Asp Ala Lys Glu Phe Glu Pro Lys Asp Val Leu Pro Asn Gly Asp Gly
225                 230                 235                 240

Thr Tyr Gln Gly Trp Ile Thr Leu Ala Val Pro Pro Gly Glu Glu Gln
            245                 250                 255

Arg Tyr Thr Cys Gln Val Glu His Pro Gly Leu Asp Gln Pro Leu Ile
            260                 265                 270

Val Ile Trp Glu
            275

(2) INFORMATION FOR SEQ ID NO: 3:

(i) SEQUENCE CHARACTERISTICS:
        (A) LENGTH: 276 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Arg Leu Leu Arg Ser His Ser Leu His Tyr Leu Phe Met Gly Ala Ser
1               5                   10                  15

Glu Gln Asp Leu Gly Leu Ser Leu Phe Glu Ala Leu Gly Tyr Val Asp
            20                  25                  30

Asp Gln Leu Phe Val Phe Tyr Asp His Glu Ser Arg Arg Val Glu Pro
            35                  40                  45

Arg Thr Pro Trp Val Ser Ser Arg Ile Ser Ser Gln Met Trp Leu Gln
    50                  55                  60

Leu Ser Gln Ser Leu Lys Gly Trp Asp His Met Phe Thr Val Asp Phe
65                  70                  75                  80

Trp Thr Ile Met Glu Asn His Asn Ala Ser Lys Glu Ser His Thr Leu
            85                  90                  95

Gln Val Ile Leu Gly Cys Glu Met Gln Glu Asp Asn Ser Thr Glu Gly
            100                 105                 110

Tyr Trp Lys Tyr Gly Tyr Asp Gly Gln Asp Ala Leu Glu Phe Cys Pro
            115                 120                 125

Asp Thr Leu Asp Trp Arg Ala Ala Glu Pro Arg Ala Trp Pro Thr Lys
    130                 135                 140

Leu Glu Trp Glu Arg His Lys Ile Arg Ala Arg Gln Asn Arg Ala Tyr
145                 150                 155                 160

Leu Glu Arg Asp Cys Pro Ala Gln Leu Gln Gln Leu Leu Glu Leu Gly
            165                 170                 175

Arg Gly Val Leu Asp Gln Gln Val Pro Pro Leu Val Lys Val Thr His
            180                 185                 190

His Val Thr Ser Ser Val Thr Thr Leu Arg Cys Arg Ala Leu Asn Tyr
            195                 200                 205

Tyr Pro Gln Asn Ile Thr Met Lys Trp Leu Lys Asp Lys Gln Pro Met
    210                 215                 220

Asp Ala Lys Glu Phe Glu Pro Lys Asp Val Leu Pro Asn Gly Asp Gly
225                 230                 235                 240

Thr Tyr Gln Gly Trp Ile Thr Leu Ala Val Pro Pro Gly Glu Glu Gln
            245                 250                 255

-continued

```
Arg Tyr Thr Cys Gln Val Glu His Pro Gly Leu Asp Gln Pro Leu Ile
            260                 265                 270

Val Ile Trp Glu
        275

(2) INFORMATION FOR SEQ ID NO: 4:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 4:

Arg Leu Leu Arg Ser His Ser Leu His Tyr Leu Phe
 1               5                  10

(2) INFORMATION FOR SEQ ID NO: 5:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO: 5:

Ile Gln Arg Thr Pro Lys Ile Gln Val Tyr Ser Arg
 1               5                  10
```

METHODS AND COMPOSITIONS FOR DIAGNOSIS AND TREATMENT OF IRON OVERLOAD DISEASES AND IRON DEFICIENCY DISEASES

The present application is a continuation of application Ser. No. 10/092,404, filed Mar. 4, 2002, now U.S. Pat. No. 7,119,170, which is a divisional of application Ser. No. 09/094,964, filed Jun. 12, 1998, now U.S. Pat. No. 6,391,852, which is a continuation-in-part of application Ser. No. 08/876,010, filed Jun. 13, 1997, abandoned, which are incorporated by reference herein in their entireties.

BACKGROUND OF THE INVENTION

Hereditary hemochromatosis (HH) is a common disease characterized by excess iron deposition in the major organs of the body (Dadone, M. M. et al. *AM. J. Clin. Pathol.* 78:196-207 (1982); Edwards, C. Q. et al. *N. Engl. J. Med.* 18:1355-1362. (1988); McLaren, C. E., et al. *Blood* 86:2021-2027 (1995); Bothwell, T. H. et al., *The metabolic and molecular basis of inherited disease* (ed. C. R. Scriver, E.A.) 2237-2269 (McGraw-Hill, New York, 1995); Bacon, B. R. et al., *Hepatology. A textbook of liver disease* (eds. Zakim, D. & Boyer, T. D.) 1439-1472 (W.B. Saunders, Philadelphia, 1996). A candidate gene for this disease, HFE, was identified by positional cloning (Feder, J. N., et al. *Nature Genetics* 13:399-408 (1996)). The gene, a novel member of the MHC class I family, was found to have a mutation, cysteine 282→tyrosine (C282Y), in 83% of patient chromosomes (Feder, J. N., et al. *Nature Genetics* 13:399-408 (1996)). This mutation eliminates the ability of HFE to associate with $\beta_2$-microglobulin ($\beta_2$m) and prevents cell-surface expression (Feder, J. N., et al., *J. Biol. Chem.* 272:14025-14028 (1997)). However, the relationship of this class I-like molecule to the regulation of iron metabolism has remained obscure.

Thus, an object of the instant invention is to provide a molecular basis for the relationship of HFE to iron metabolism, and diagnostic and therapeutic agents for the treatment of iron overload diseases and iron deficiency diseases.

SUMMARY OF THE INVENTION

One aspect of the invention is a method of treating an iron overload disease by administering to a patient an HFE polypeptide having the sequence of SEQ ID NO:1,

```
RLLRSHSLHYLFMGASEQDLGLSLFEALGYVDDQLFVFYDHESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE,
``` wherein the HFE polypeptide is provided in a complex with full length, wild type human $\beta_2$m.

A further aspect of the invention is a composition of an HFE polypeptide having the amino acid sequence of SEQ ID NO:1,

```
RLLRSHSLHYLFMGASEQDLGLSLFEALGYVDDQLFVFYDHESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE,
``` wherein the HFE polypeptide is provided in a complex with full length, wild type human $\beta_2$m.

A further aspect of the invention is a method of treating an iron deficiency disease by administering to a patient an HFE polypeptide, i.e., H63D-HFE mutant, having the sequence of SEQ ID NO:2,

```
RLLRSHSLHYLFMGASEQDLGLSLFEALGYVDDQLFVFYDHESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE,
``` wherein the HFE polypeptide is provided in a complex with full length, wild type human $\beta_2$m.

A further aspect of the invention is a composition of an HFE polypeptide, i.e., H63D-HFE mutant, having the amino acid sequence of SEQ ID NO:2,

```
RLLRSHSLHYLFMGASEQDLGLSLFEALGYVDDQLFVFYDHESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE,
``` wherein the HFE polypeptide is provided in a complex with full length, wild type human $\beta_2$m.

A further aspect of the invention is a method of treating an iron deficiency disease by administering to a patient an HFE polypeptide, i.e., H111A/H145A-HFE mutant, having the sequence of SEQ ID NO:3,

```
RLLRSHSLHYLFMGASEQDLGLSLFEALGYVDDQLFVFYDHESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE,
``` wherein the HFE polypeptide is provided in a complex with full length, wild type human $\beta_2$m.

A further aspect of the invention is a composition of an HFE polypeptide, i.e., H111A/H145A-HFE mutant, having the amino acid sequence of SEQ ID NO:3,

```
RLLRSHSLHYLFMGASEQDLGLSLFEALGYVDDQLFVFYDHESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE,
``` wherein the HFE polypeptide is provided in a complex with full length, wild type human $\beta_2$m.

BRIEF DESCRIPTION OF THE FIGURES

(FIG. 1A) HFE antibodies immunoprecipitate 12, 49, 100, and 200 kDa surface-labeled proteins from wild-type HFE expressing cells but not from parental 293 or C282Y HFE mutant expressing cells. (FIG. 1B) FLAG epitope antibodies also immunoprecipitate 12, 49, 100, and 200 kDa surface-labeled proteins in wild-type HFE expressing cells but not parental 293 or C282Y HFE mutant expressing cells. (FIG. 1C) TfR antibodies immunoprecipitate 100 and 200 kDa surface-labeled proteins from parental 293, wild-type and C282Y HFE expressing cells and in addition, detect $\beta_2$m (12 kDa) and HFE (49 kDa) proteins only in wild-type HFE expressing cells. (FIG. 1D) HLA-ABC antibodies fail to immunoprecipitate 100 and 200 kDa proteins from parental 293 cells.

(FIG. 2A) HFE antibodies co-immunoprecipitate TfR from wild-type and H63D HFE expressing cells but not 293 or C282Y HFE mutant expressing cells. (FIG. 2B) HFE antibodies immunoprecipitate similar amounts of HFE protein from wild-type, C282Y and H63D HFE expressing cells. (FIG. 2C) TfR antibodies co-immunoprecipitate HFE from wild-type and H63D HFE expresser cells but not parental 293 or C282Y mutant expressing cells. (FIG. 2D) TfR antibodies immunoprecipitate similar amounts of TfR protein from parental 293, and wild-type, C282Y and H63D HFE expressing cells. (FIG. 2E) FLAG epitope (M2) antibodies co-immunoprecipitate TfR from wild-type and H63D HFE expressing cells but not parental 293 or C282Y HFE mutant expressing cells.

(FIG. 3A) Transferrin binding to TfR in cells that over-express the C282Y mutant protein (intracellular) (inset). Cells (clone 10 open squares and clone 12, closed squares) were incubated with various concentrations of transferrin at 37° C. for 20 mins. The data represent the mean of duplicate determinations corrected for non-specific binding. Scatchard analysis revealed an apparent $K_D$ of approximately 14 and 12 nM respectively, with the number of apparent transferrin binding sites of $2 \times 10^5$ and $3 \times 10^5$ per cell. (FIG. 3B) Binding of $^{125}$I-transferrin to two clones of 293 cells overexpressing the wild type (surface) form of HFE (clone 7, open circles; clone 3, closed circles) Saturation of the transferrin receptors occurred at approximately the same concentration as in (FIG. 3A), however, the amount of transferrin bound was reduced 2-4 fold (inset). Scatchard analysis revealed that the affinity for transferrin had been reduced to 180 and 40 nM, and number of apparent transferrin binding sites of $9.0 \times 10^4$ to $2.5 \times 10^5$ per cell. (FIG. 3C) Binding of $^{125}$I-transferrin to 293 cells in the presence of soluble HFE/$\beta_2$m heterodimers. 293 cells bind transferrin at 37° C., with an apparent $K_D$ of 19 nM (open squares), whereas in the presence of 2 μM of soluble HFE/$\beta_2$m heterodimers, the $K_D$ is reduced 5 fold to 100 nM (open triangles). Control experiments using an identical amount of an MHC class I, H-2K$^d$ 15 protein complexed with human $\beta_2$m failed to have any affect of transferrin binding (closed circles).

SPECIFIC EMBODIMENTS OF THE INVENTION

Figure 1:
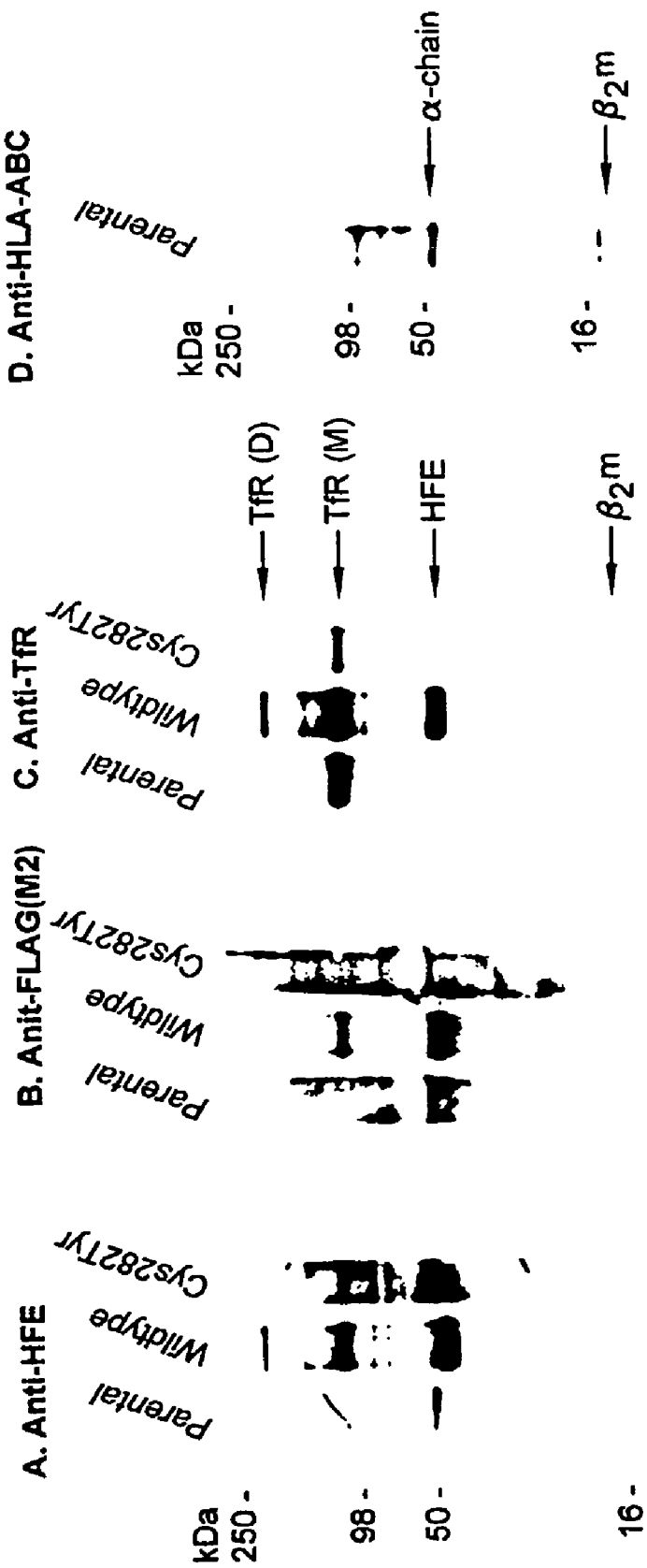
FIG. 1A-1D. Cell-surface labeling of HFE and association with TfR.

In some embodiments of the invention, HFE polypeptides are provided for therapeutic use in patients having symptoms of a primary iron overload disease or syndrome, such as hemochromatosis, or other iron overload condition caused by secondary causes, such as repeated transfusions. The HFE polypeptide can be full length HFE or some fragment of HFE. Preferably, the HFE polypeptide comprises the extracellular portion of the HFE. The predicted amino acid sequence and genomic and cDNA sequences of HFE (also denoted HH in some publications) were provided in (Feder, J. N., et al. *Nature Genetics* 13:399-408 (1996); Ruddy et al., *Genome Res.* 7:441-456 (1997)), hereby incorporated by reference in its entirety. The HFE polypeptides may be administered with β-2-microglobulin, such as in the form of a complex. In some embodiments, HFE polypeptides greater than about 20 amino acids are administered in a complex with β-2-microglobulin.

In some embodiments of the invention, agonists or antagonists of the HFE protein or transferrin receptor are provided. Agonists of the HFE polypeptide, and/or antagonists of the transferrin receptor, are useful for example, in the treatment of primary or secondary iron overload diseases or syndromes, while antagonists of the HFE polypeptide, or agonists of the transferrin receptor are useful, for example, in the treatment of iron deficiency conditions, such as anemias. In other embodiments, mutant HFE proteins are provided which function as antagonists of the wild-type HFE protein. In a specific embodiment illustrated by working examples HFE antagonists include a soluble truncated HFE polypeptide in which a His residue is substituted by an Asp residue at position 63, and a soluble truncated HFE polypeptide in which His residues at positions 111 and 145 are substituted by an Ala residue. Antagonists or agonists can also be antibodies, preferably monoclonal antibodies, directed against the transferrin receptor or extracellular region of the HFE polypeptide. In some embodiments of the invention, HFE polypeptides can serve as antagonists of the transferrin receptor. In further embodiments of the invention, peptidomimetics can be designed using techniques well known in the art as antagonists or agonists of the HFE protein and/or the transferrin receptor.

Ligands for the transferrin receptor, whether antagonists or agonists, can be screened using the techniques described herein for the ability to bind to the transferrin receptor. Additionally, competition for HFE binding to the receptor can be done using techniques well known in the art. Ligands, or more generally, binding partners for the HFE polypeptide can be screened, for example, for the ability to inhibit the complexing of the HFE polypeptide to β-2-microglobulin, using techniques described herein.

In some embodiments of the invention, agonists or antagonists of transferrin are similarly utilized to increase or decrease the amount of iron transported into a cell, such as into a patient's hepatocytes or lymphocytes.

For example, the efficacy of a drug, therapeutic agent, agonist, or antagonist can be identified in a screening program in which modulation is monitored in vitro cell systems. Host cell systems which express various mutant HFE proteins (especially the 24d1 and 24d2 mutations) and are suited for use as primary screening systems. Candidate drugs can be evaluated by incubation with these cells and measuring cellular functions dependent on the HFE gene or by measuring proper HFE protein folding or processing. Such assays might also entail measuring receptor-like activity, iron transport and metabolism, gene transcription or other upstream or downstream biological function as dictated by studies of HFE gene function.

Alternatively, cell-free systems can also be utilized. Purified HFE protein can be reconstituted into artificial membranes or vesicles and drugs screened in a cell-free system. Such systems are often more convenient and are inherently more amenable to high throughput types of screening and automation.

In some embodiments of the invention, the HFE protein can be purified by one of several methods which have been selected based upon the molecular properties revealed by its sequence and its homology to MHC Class I molecules. Since the molecule possesses properties of an integral membrane protein, i.e. contains a transmembrane domain, the protein is preferably first isolated from the membrane fraction of cells using detergent solubilization. A variety of detergents useful for this purpose are well known in the art.

Once solubilized, the HFE protein can be further purified by conventional affinity chromatography techniques. The conventional approaches of ion exchange, hydrophobic interaction, and/or organomercurial chromatographies can be utilized. These methodologies take advantage of natural features of the primary structure, such as: charged amino acid residues, hydrophobic transmembrane domains, and sulfhydryl-containing cysteine residues, respectively. In the affinity chromatography approach use is made of immunoaffinity ligands or of the proposed interaction of the HFE protein with β-2-microglobulin, calnexin or similar molecules. In the former, the affinity matrix consists of antibodies (polyclonal or monoclonal) specific to the HFE protein coupled to an inert matrix. The production of antibodies specific to the HFE protein can be performed using techniques well known in the art. In the latter method, various ligands which are proposed to specifically interact with the HFE protein based on its homology with MHC Class I molecules could be immobilized on an inert matrix. For example, β-2-microglobulin, β-2-microglobulin-like molecules, or other specific proteins such as calnexin or calnexin-like molecules, and the like, or portions and/or fragments thereof, can be utilized. General methods for preparation and use of affinity matrices are well known in the art.

Criteria for the determination of the purity of the HFE protein include those standard to the field of protein chemistry. These include N-terminal amino acid determination, one and two-dimensional polyacrylamide gel electrophoresis, and silver staining. The purified protein is useful for use in studies related to the determination of secondary and tertiary structure, as aid in drug design, and for in vitro study of the biological function of the molecule.

In some embodiments of the invention, drugs can be designed to modulate HFE gene and HFE protein activity from knowledge of the structure and function correlations of HFE protein and from knowledge of the specific defect in various HFE mutant proteins. For this, rational drug design by use of X-ray crystallography, computer-aided molecular modeling (CAMM), quantitative or qualitative structure-activity relationship (QSAR), and similar technologies can further focus drug discovery efforts. Rational design allows prediction of protein or synthetic structures which can interact with and modify the HFE protein activity. Such structures may be synthesized chemically or expressed in biological systems. This approach has been reviewed in Capsey et al., Genetically Engineered Human Therapeutic Drugs, Stockton Press, New York (1988). Further, combinatorial libraries can be designed, synthesized and used in screening programs.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The present invention also relates to the use of polypeptide or protein replacement therapy for those individuals determined to have a defective HFE gene. Treatment of HH disease can be performed by replacing the defective HFE protein with normal protein or its functional equivalent in therapeutic amounts. A therapeutic amount of an HFE polypeptide for "replacement therapy", an HFE agonist, or transferrin receptor antagonist is an amount sufficient to decrease the amount of iron transported into a cell. Preferably, the cell is a lymphocyte.

Similarly, a therapeutic amount of an HFE antagonist or transferrin receptor agonist is an amount sufficient to increase the amount of iron transported into a cell.

HFE polypeptide can be prepared for therapy by any of several conventional procedures. First, HFE protein can be produced by cloning the HFE cDNA into an appropriate expression vector, expressing the HFE gene product from this vector in an in vitro expression system (cell-free or cell-based), and isolating the HFE protein from the medium or cells of the expression system. General expression vectors and systems are well known in the art. In addition, the invention envisions the potential need to express a stable form of the HFE protein in order to obtain high yields and obtain a form readily amenable to intravenous administration. Stable high yield expression of proteins have been achieved through systems utilizing lipid-linked forms of proteins as described in wettstein et al. *J Exp Med* 174:219-228 (1991) and Lin et al. *Science* 249:677-679 (1990).

HFE protein or portions thereof can be prepared synthetically. Alternatively, the HFE protein can be prepared from total protein samples by affinity chromatography. Sources would include tissues expressing normal HFE protein, in vitro systems (outlined above), or synthetic materials. The affinity matrix would consist of antibodies (polyclonal or monoclonal) coupled to an inert matrix. In addition, various ligands which specifically interact with the HFE protein could be immobilized on an inert matrix, such as β-2-microglobulin or portions thereof, β-2-microglobulin-like molecules, or other specific proteins such as calnexin and calnexin-like molecules or portions thereof. General methods for preparation and use of affinity matrices are well known in the art.

Protein replacement therapy requires that HFE polypeptides be administered in an appropriate formulation. The HFE polypeptides can be formulated in conventional ways standard to the art for the administration of protein substances. Delivery may require packaging in lipid-containing vesicles (such as Lipofectin™ or other cationic or anionic lipid or certain surfactant proteins) that facilitate incorporation into the cell membrane. The HFE protein formulations can be delivered to affected tissues by different methods depending on the affected tissue. For example, iron absorption is initiated in the GI tract. Therefore, delivery by catheter or other means to bypass the stomach would be desirable. In other tissues, IV delivery will be the most direct approach.

The following examples are provided to illustrate certain aspects of the present invention and not intended as limiting the subject matter thereof:

EXPERIMENTAL EXAMPLES

A. Introduction

In this experimental example, we demonstrated that HFE forms a stable complex with the transferrin receptor (TfR), the molecule responsible for receptor-mediated endocytosis of iron-bound transferrin. This interaction, assessed both in cultured cells by over-expression of HFE and also by addition of soluble HFE/$\beta_2$m heterodimers, causes a decrease in the apparent affinity of the TfR for transferrin. In contrast, the disease-causing mutation (C282Y) fails to form this TfR complex permitting high affinity binding of transferrin. These results established the first molecular link between HFE and iron absorption and indicate that an altered regulation of transferrin-dependent iron uptake leads to HFE disease.

B. Methods

1. Cell surface protein biotinylations. Cells (4×10$^6$) were seeded into 100 mm dishes and grown overnight to 80% confluency. The plates were moved to 4° C. and gently washed four times with PBS. Suflo-NHS-LC Biotin (Pierce) was added in PBS to a final concentration of 500 µg/ml and incubated on ice for 30 mins. The Biotin reagent was removed and the plates washed 4 times with PBS containing 50 mM glycine. Cells were lysed in 500 ml of 25 mM Tris-HCL, pH 7.5 150 mM NaCl plus 0.5% NP-40. Protein concentrations were determined by BCA assay (Pierce) and one mg of protein was pre-cleared with Protein-G-Sepharose (Pharmacia) and immunoprecipitated with either 10 mg of an anti-HFE rabbit polyclonal antibody (CT1) (Feder, J. N., et al. *J. Biol. Chem.* 272:14025-14028 (1997)), 50 µg of FLAG (M2) monoclonal antibody (Kodak), 5 µg of transferrin receptor monoclonal antibody (Caltag) or 10 µg of HLA-ABC antibody (Immunotech). Precipitated proteins were separated on 4-20% Tris-glycine polyacrylamide gels (Novex), electroblotted to PVDF membranes (Novex) and biotinylated proteins were visualized with 2 µg/ml of streptavidin-HRP (Pierce) followed by ECL detection reagents (Amersham).

2. Immunoprecipitations and western blotting. Cells were lysed in the same buffer as above and precipitations carried out with the same antibodies and concentrations except that no pre-clearing step was carried out. Precipitated proteins were separated and electroblotted to PVDF membranes as previously described (Feder, J. N., et al. *J. Biol. Chem.* 272:14025-14028 (1997).

3. Transferrin binding assays. Transferrin binding assays were carried out as essentially as described (Ward, J. H. et al., *J. Biol. Chem.* 257:10317-10323 (1982)) with the following modifications. Cells were seeded at a density of 6×10$^5$ per well in 6-well dishes coated with 0.01% fibronectin (Sigma) and grown overnight. Cells were washed 1 time with 2 ml of DME-H21 media containing 1% FBS and then incubated at either 37° C. or on ice with varying concentrations of transferrin which include [$^{125}$I]-diferric transferrin (1 mCi/mg) (NEN) as a tracer ($\frac{1}{30}^{th}$ of the final concentration) in a final volume of 750 µl. To determine the amount of non-specific transferrin binding, cells were simultaneously incubated under the same conditions but in the presence of 100 times the molar concentration of cold holo-transferrin (Sigma). After 20 mins (37° C.) or 90 mins (4° C.), the media was removed and counted in a Beckman 9600 scintillation counter. The cells were incubated on ice and washed 2 times with media containing 1% FBS, and then lysed with 1% SDS and counted. Specific binding was calculated by substracting the non-specific binding from the total binding. A second method was also used that utilized a constant amount of labeled transferrin (10 nm) and increasing amount of unlabeled transferrin to increase the total transferrin concentration. Identical results to those produced by the first method were obtained.

4. Expression and Purification of Secreted HFE. A secreted HFE/62$_2$m heterodimer was constructed as follows, wherein the amino acid sequence of the HFE is shown (SEQ ID NO:1):

```
RLLRSHSLHYLFMGASEQDLGLSLFEALGYVDDQLFVFYDHESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE
```

A 5' Xho I site, a stop codon after the codon corresponding to amino acid 298 (residue 276 of the mature protein) and a 3' Not I site were inserted in the HFE gene by site-directed mutagenesis. After verifying the sequence, the modified HFE gene was subcloned into the expression vector PBJ5-GS that carries the glutamine synthetase gene as a selectable marker and as a means of gene amplification in the presence of the drug methionine sulfoximine (Bebbingtion, C. R. & Hentschel, C. G. G. in *DNA Cloning: A Practical Approach.* (ed. Glove, D M) 163-188 (Oxford: IL, 1987)). The HFE expression plasmid was cotransfected with a human $\beta_2$m expression vector (i.e., full length, wild type gym, Fahnestock, M. L., et al. *Immunity* 3:583-590 (1995)) into CHO cells. Cell lines secreting HFE/$\beta_2$m heterodimers were identified by immunoprecipitation of supernatants of $^{35}$S-methionine metabolically labeled cells using an antibody against human $\beta_2$m (BBM.1) (Parham, P. et al., *J. Biol. Chem.* 258:6179-6186 (1983)). A protein of molecular mass of 43 kDa was co-immunoprecipitated with labeled $\beta_2$m from the supernatants, and was verified to be the truncated HFE polypeptide chain by N-terminal sequencing of the purified protein (yielding the sequences RLLRSHSLHYLF (SEQ ID NO:4) and IQRTPKIQVYSR (SEQ ID NO:5) corresponding to the correctly processed mature forms of HFE and human gym; data not shown). Soluble HFE/$\beta_2$m heterodimers were purified on a BBM.1 immunoaffinity column, followed by separation of free $\beta_2$m from the heterodimers on a Superdex™ 75 HR 10/30 FPLC gel filtration column or by using an immunoaffinity column constructed with an HFE monoclonal antibody raised against the purified heterodimer. 0.25 mg of purified secreted HFE, FcRn and UL18 were treated with acetic acid and analysed for the presence of bound peptides using established methods (Rotzschke, O., et al. *Nature* 348:252-257 (1990)) as previously described for UL18 (Fahnestock, M. L., et al. *Immunity* 3:583-590 (1995)) and FcRn (Raghavah, M. et al., *Biochemistry* 32:8654-8660 (1993)). Acid eluates were analyzed by Edman degradation using an Applied Biosystems Model 477A protein sequencer for pool sequencing (Table 1). In order to detect N-terminally blocked peptides, the HFE and FcRn eluates were analyzed by matrix-assisted, laser desorption, time-of-flight mass spectrometry using a PersSeptive Biosystems ELITE mass spectrometer.

Site-directed mutation was used to introduce a missense mutation to the HFE gene to produce HFE protein in which His-63 is replaced by an aspartic acid residue. The H63D mutant HFE gene was expressed in CHO cells and secreted H63D-HFE/$\beta_2$m heterodimers were purified. The amino acid sequence of the H63D-HFE protein is shown (SEQ ID NO:2):

```
RLLRSHSLHYLFMGASEQDLGLSLFEALGYVDDQLFVFYDDESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE
```

The role of two His residues, i.e., His-111 and His-145, in HFE-TfR binding was also analyzed by replacing both residues with an Ala residue through site-directed mutagenesis, yielding a soluble H111A/H145A mutant. The amino acid sequence of the H111A/H145A-HFE protein is shown (SEQ ID NO:3):

```
RLLRSHSLHYLFMGASEQDLGLSLFEALGYVDDQLFVFYDHESRRVEPRT
PWVSSRISSQMWLQLSQSLKGWDHMFTVDFWTIMENHNHSKESHTLQVIL
GCEMQEDNSTEGYWKYGYDGQDHLEFCPDTLDWRAAEPRAWPTKLEWERH
KIRARQNRAYLERDCPAQLQQLLELGRGVLDQQVPPLVKVTHHVTSSVTT
LRCRALNYYPQNITMKWLKDKQPMDAKEFEPKDVLPNGDGTYQGWITLAV
PPGEEQRYTCQVEHPGLDQPLIVIWE
```

TABLE 1 pmole of amino acids recovered from acid elutions.

| Cycle number | HFE | FcRn | UL18 |
|---|---|---|---|
| 1 | 2.1 | 5.9 | 86.0 |
| 2 | 0.5 | 4.7 | 75.1 (Leu, Met = 71) |
| 3 | 0.4 | 0.7 | 36.9 (Pro = 19) |
| 4 | 0.8 | 7.6 | 19.8 |
| 5 | 0.0 | 0.0 | 11.3 |
| 6 | 3.5 | 0.0 | 4.0 |
| 7 | 1.0 | 0.2 | 3.7 |
| 8 | 0.0 | 0.6 | 6.5 |
| 9 | 1.9 | 9.5 | 4.3 |
| 10 | 0.0 | 0.3 | 1.3 |

The total yield of amino acids from each sequencing cycle ispresented for acid eluates derived from equivalent amount of solubleHFE, FcRN and UL18 heterodimers. Only those amino acid residues thatshowed an increase in the absolute amount recovered compared to theprevious cycle were considered significant. Results for the FcRn andUL18 eluates are similar to those previously reported (Fahnestock,M. L., et al. Immunity 3: 583-590 (1995); Raghavah, M. et al.,Biochemistry 32: 8654-8660 (1993)) in which UL18, but not FcRn,was shown to bind endogenous peptides.

C. Results and Discussion

To investigate the role of HFE in the regulation of iron metabolism, we utilized cell-surface labeling to detect potential HFE interactive proteins. Human embryonic kidney cells (293 cells), engineered to over-express either wild-type or mutant forms of HFE, were treated with biotin-conjugated N-hydroxysuccinimide (NHS-biotin) to label proteins expressed on the cell-surface. Subsequently, total cell lysates were immunoprecipitated with previously characterized antibodies directed toward the C-terminal peptide sequence of HFE or monoclonal antibodies against the FLAG epitope tag which had been engineered into the HFE protein (Feder, J. N., et al. *J. Biol. Chem.* 272:14025-14028 (1997)). Biotinylated proteins were detected with streptavidin-conjugated horseradish peroxidase (HRP). Lysates from parental 293 cells displayed little surface-labeling in accordance with previous results, demonstrating undetectable levels of HFE protein in these cells (FIGS. 1A and B) (Feder, J. N., et al. *J. Biol. Chem.* 272:14025-14028 (1997)). In contrast, prominent bands of 12, 49, 100 and 200 kDa were observed in lysates from cells overexpressing the wild-type HFE; these bands were absent from immunoprecipitates from cells overexpressing the C282Y mutant form of HFE (FIGS. 1A and B). In previous studies demonstrated that the plasma membrane-bound form of HFE was 49 kDa in molecular mass and associated with $\beta_2$m, a 12 kDa protein (Feder, J. N., et al. *J. Biol. Chem.* 272:14025-14028 (1997)). The presence of 49 and 12 kDa labeled bands in HFE-specific immune-complexes from wild-type HFE expressing cells and their absence in parental and C282Y mutant expressing cells is consistent with their identity as HFE and him. The failure of the 100 and 200 kDa proteins to be co-immunoprecipitated from the C282Y mutant expressing cells indicates a specific interaction of these proteins with the cell-surface form of HFE.

To determine the specificity of these protein interactions with HFE, we performed immunoprecipitations with antibodies that recognize the related HLA-A, B and C proteins. These antibodies detected proteins at approximately 45 kDa and 12 kDa, the predicted molecular masses of HLA heavy chain and $\beta_2$m, but failed to co-immunoprecipitate the 100 and 200 kDa bands (FIG. 1D).

To identify the 100 and 200 kDa proteins which co-immunoprecipitated with HFE, we investigated proteins known to participate in iron homeostasis. Interestingly, the major carrier of transferrin-bound iron, the transferrin receptor (TfR) is known to display a characteristic pattern of monomers and dimers migrating at approximately 100 and 200 kDa in denaturing gel electrophoresis (Seligman, P. A. et al. *J. Biol. Chem.* 254:9943-9946 (1979); Wada, H. G. et al., *J. Biol. Chem.* 254:12629-12635 (1979); Omary, M. B. et al., *J. Biol. Chem.* 256:12888-12892 (1981)). To determine whether HFE could associate with the TfR, we utilized TfR antibodies to immunoprecipitate surface-labeled proteins from the three cell lines. Two prominent proteins of molecular mass corresponding to the monomeric and dimeric forms of the TfR were seen in the parental 293 as well as the wild-type HFE and the C282Y mutant HFE expressing cell lines (FIG. 1C). Significantly, two proteins with masses corresponding to those of HFE and $\beta_2$m (49 kDa and 12 kDa, respectively) were observed only in lysates from the cells which overexpress wild-type HFE but not in lysates from the parental 293 or C282Y mutant protein expressing cells.

Figure 2A:
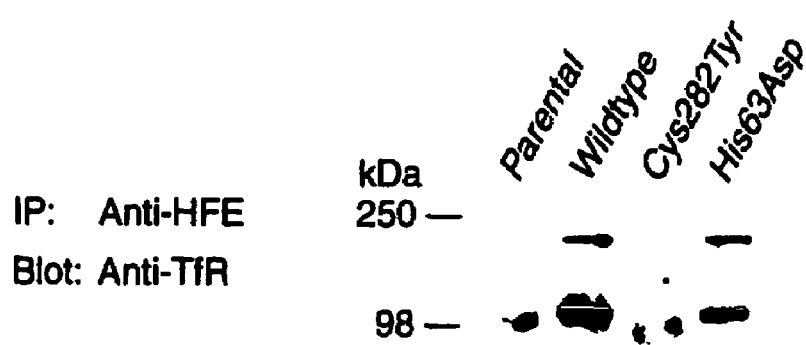
FIG. 2A-2E. Direct association of TfR with HFE.
Figure 2B:
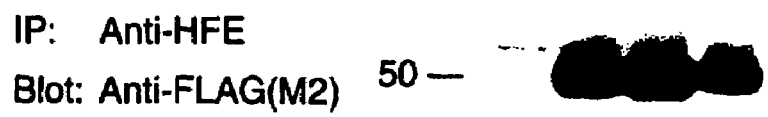
Figure 2C:
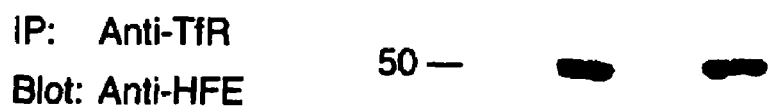
Figure 2D:
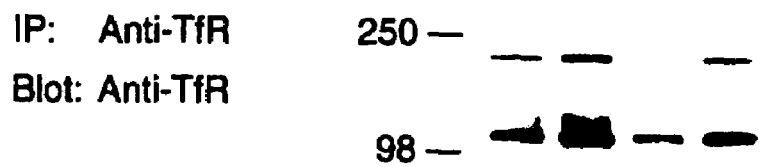
Figure 2E:
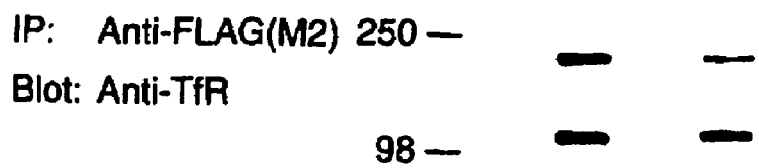

The HFE/TfR association results were corroborated by performing co-immunoprecipitation experiments on unlabeled total cell lysates. Immunoprecipitation with HFE antibodies followed by blotting and probing with antibodies to TfR demonstrated that the TfR was complexed only with the wild-type form of HFE but not with the C282Y mutant (FIG. 2A). Stripping this blot and reprobing with the FLAG epitope antibodies to detect HFE, demonstrated that equivalent amounts of HFE are being expressed and immunoprecipitated from each of the cell lines but, as expected, are absent in the parental 293 cells (FIG. 2B). Performing the inverse experiment, wherein cell lysates were first immunoprecipitated with TfR antibodies followed by blotting with HFE antibodies, revealed that HFE co-immunoprecipitated with the TfR from the wild-type expressing cells but not the C282Y or parental 293 cell lines (FIG. 2C). The absence of HFE in the parental 293 and C282Y mutant cell lines was not due to failure to precipitate TfR; reprobing the blot with TfR antibodies demonstrated that similar amounts of TfR protein were precipitated from each of the cell lines (FIG. 2D). To further control for the specificity of the HFE antibodies, we first immunoprecipitated cell lysates with FLAG epitope antibodies to specifically precipitate the HFE/FLAG fusion proteins followed by blotting with TfR antibodies. As in FIG. 2A, the TfR was co-immunoprecipitated in the wild-type HFE expressing cells but not from the C282Y mutant expressing cells (FIG. 2E). Experiments performed on an independent series of cell lines engineered to express wild-type and mutant HFE which lacked the FLAG epitope tag yielded identical results to those shown in FIG. 2A-2E when immunoprecipitations were carried out with HFE and TfR antibodies.

In immunoprecipitation experiments on unlabeled cell lysates we included as a further control another mutant of HFE wherein histidine 63 was replaced by aspartate (H63D). As with wild-type HFE, the H63D protein is also expressed on the cell surface (Feder, J. N., et al. *J. Biol. Chem.* 272:14025-14028 (1997)), however, functional effect of this mutation has yet been identified. The association of HFE with the TfR as assessed by co-immunoprecipitation appeared unaffected by the H63D mutation (FIG. 2A-E).

Figure 3A:
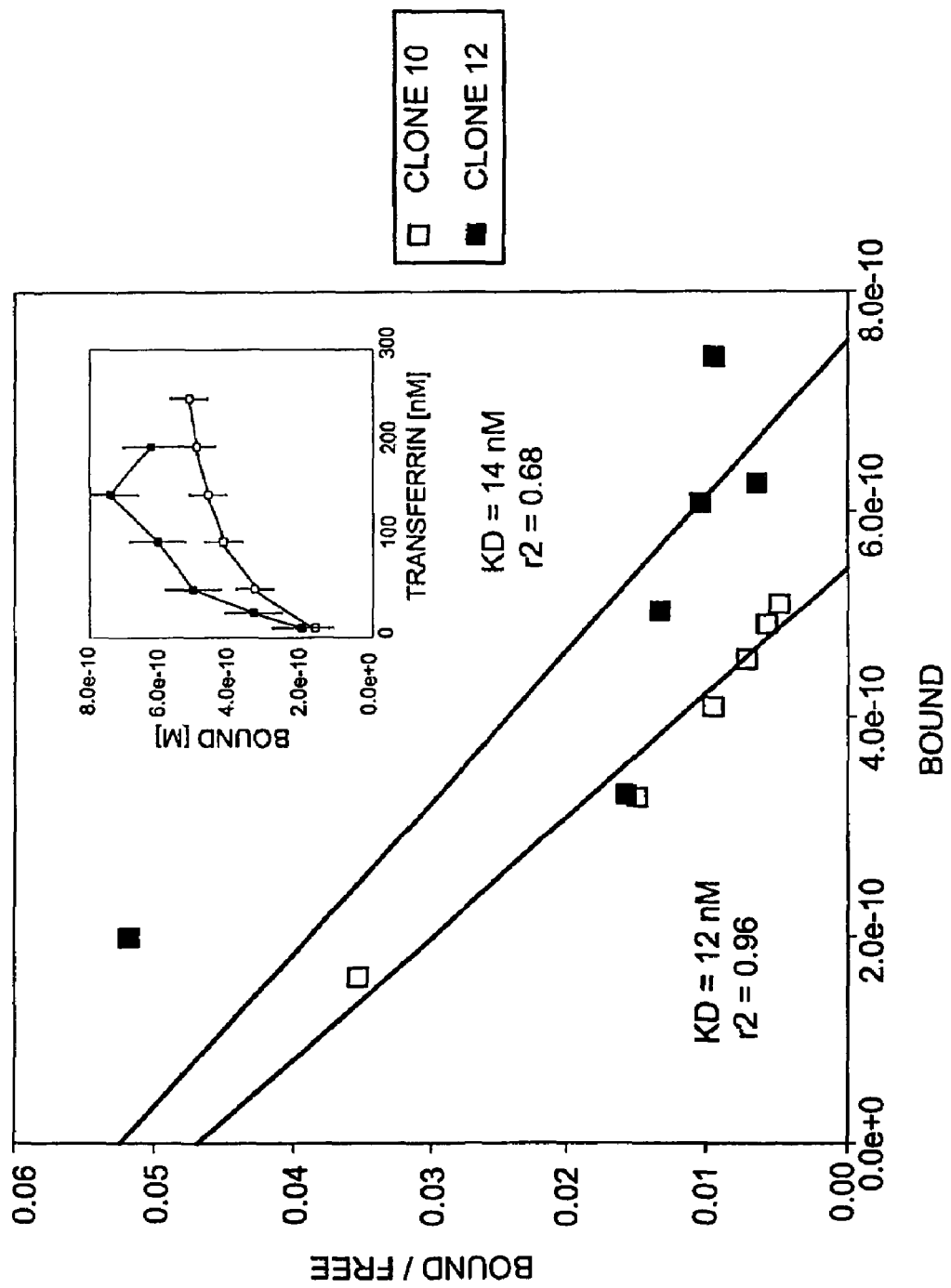
FIG. 3A-3C. Effect of HFE on $^{125}$I-transferrin binding to the TfR.
Figure 3B:
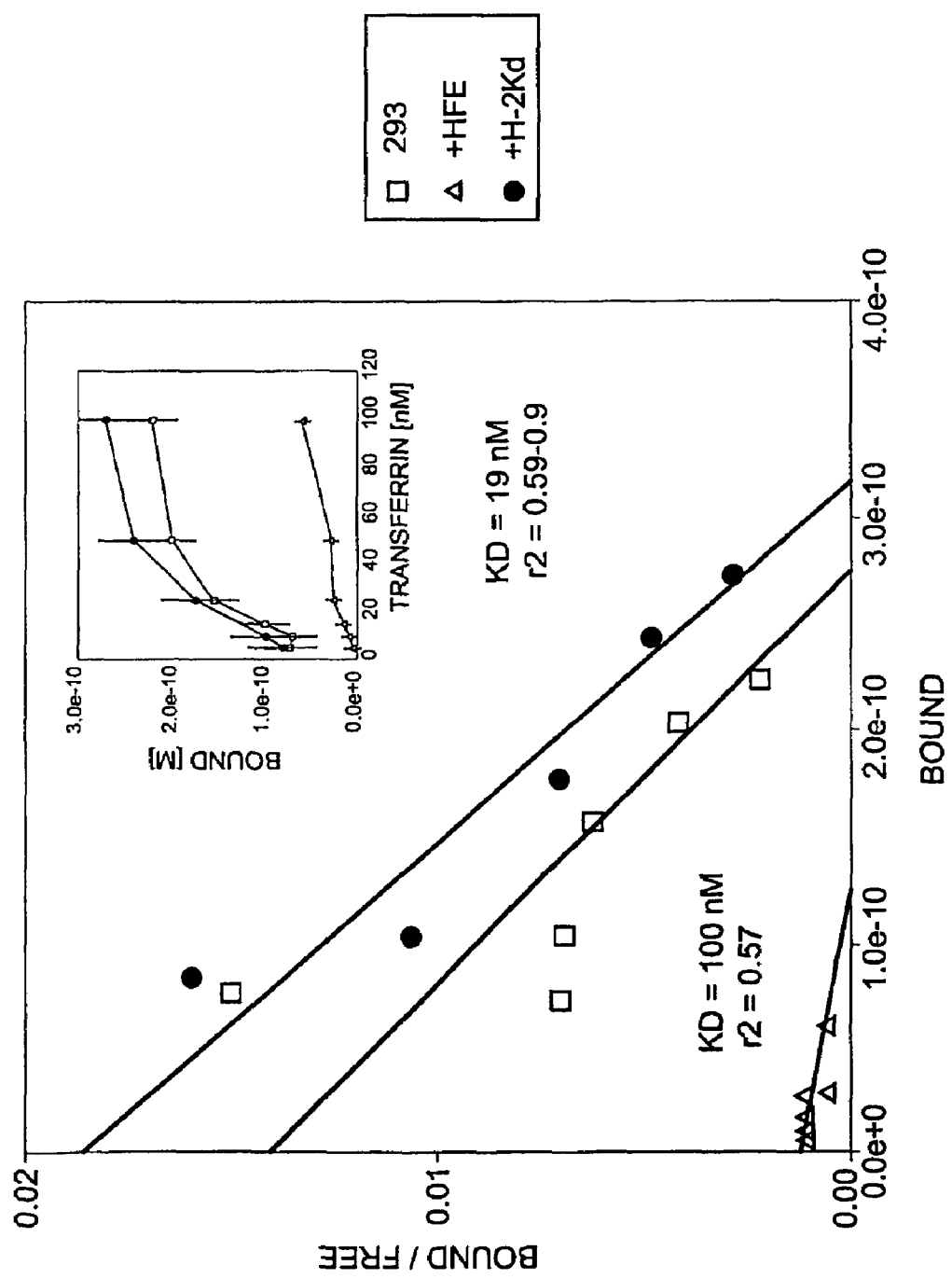

To assess the biological effect of the HFE/TfR interaction, we characterized the transferrin-binding properties of the TfR in the presence or absence of HFE. For these studies we examined [$^{125}$I]-diferric transferrin binding to intact 293 cells engineered to over-express both $\beta_2$m and the wild-type or the C282Y mutant forms of HFE. The latter served as a baseline comparison since our earlier studies demonstrated that the C282Y mutant was not expressed on the cell surface (Feder, J. N., et al. *J. Biol. Chem.* 272:14025-14028 (1997)), and failed to interact with the TfR (FIGS. 1 and 2). In addition, the C282Y cell lines, like the wild-type cell lines, were selected for in G418. The initial binding experiments were performed at 37° C., which allowed the total [$^{125}$I]-diferric transferrin bound to be representative of both surface-bound and internalized ligand (Karin, M. et al., *J. Biol. Chem.* 256:3245-3252 (1981); Octave, J. N. et al., *Eur. J. Biochem.* 123:235-240 (1982). The binding of [$^{125}$I]-diferric transferrin saturated at 150-300 nM on both C282Y mutant and wild-type HFE expressing cells (FIGS. 3A and B insets, which present data from two separate cell clones for each the wild-type and mutant HFE). When subjected to Scatchard analysis, the C282Y HFE mutant expressing clones bound transferrin with an apparent $K_D$ of approximately 12 and 14 nM and expressed approximately $2.3 \times 10^5$ and $3.3 \times 10^5$ transferrin binding sites per cell, respectively (FIG. 3A). These data were similar to values reported previously for other cultured cell lines (Mulford, C. A. et al. *J. Biol. Chem.* 263:5455-5461 (1988); Ward, J. H. et al. *J. Biol. Chem.* 257:10317-10323 (1982)), suggesting that binding and trafficking of the TfR to the cell surface in the mutant HFE-expressing cells was normal. By contrast, the affinity of the TfR for transferrin, in the wild-type HFE expressing clones, was reduced 4 and 15-fold to apparent $K_D$ values of 40 and 180 nM respectively, while expressing approximately $3.0 \times 10^5$ apparent transferrin binding sites per cell (FIG. 3B). Taken together, these results suggest that the presence or absence of the HFE protein on the cell surface affects the apparent $K_D$ of the TfR for transferrin.

Figure 3C:
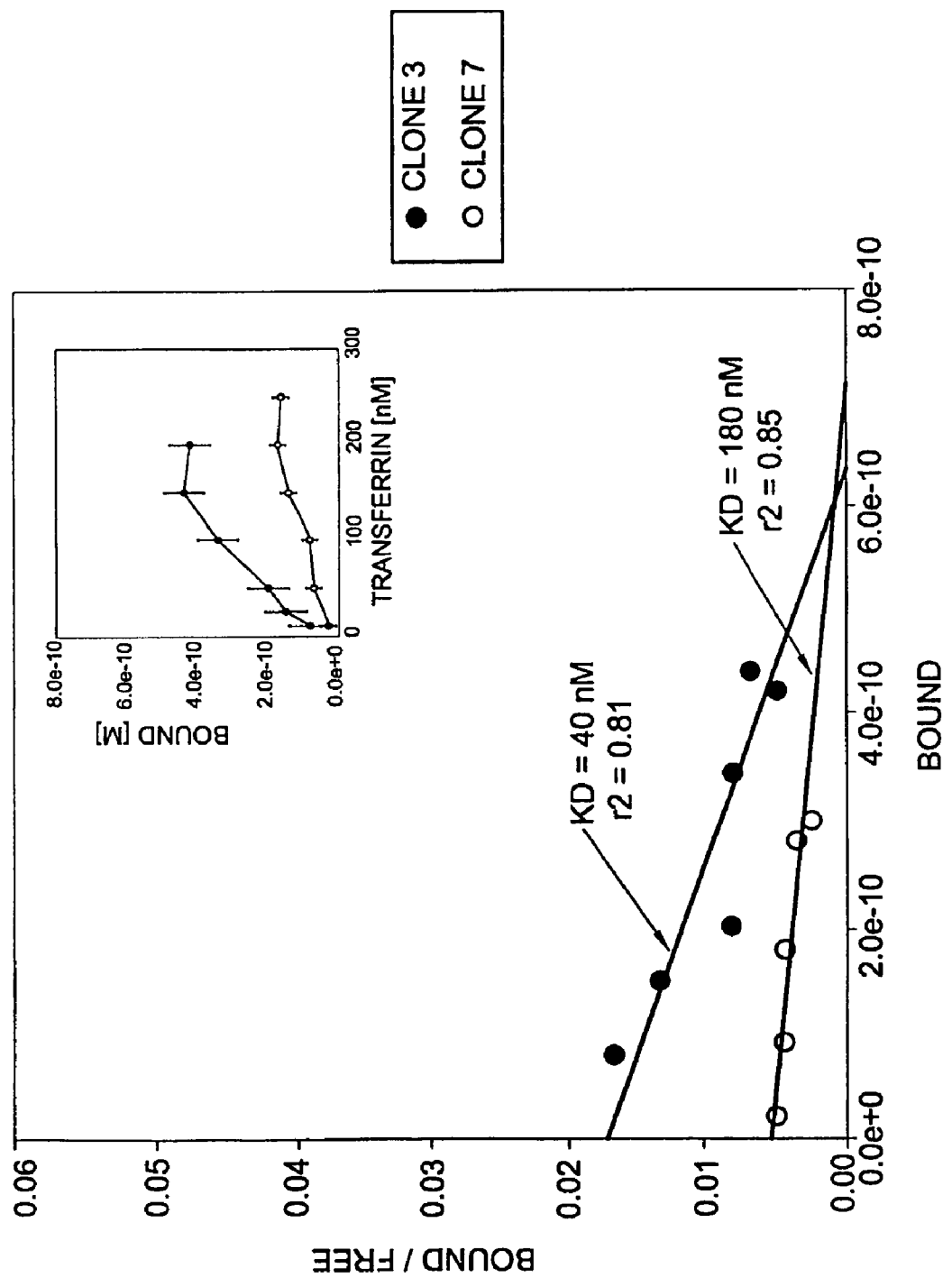

As an alternative method to assess the effect of HFE on transferrin binding to the TfR, we added a soluble form of HFE/$\beta_2$m heterodimer to the culture medium of parental 293 cells. At 37° C. the binding of transferrin to parental 293 cells occurred with an apparent $K_D$ of 19 nM. In contrast, the apparent $K_D$ for the binding of transferrin to the TfR in the presence of 2 μM soluble HFE/$\beta_2$m heterodimer was reduced 5-fold to 100 nM. The apparent number of transferrin binding sites was also reduced from $1.25 \times 10^5$ to $5.0 \times 10^4$ per cell, a reduction of 60% (FIG. 3C), suggesting that the rate of receptor internalization without bound transferrin may be increased in the presence of HFE. To determine whether the regulation of the apparent $K_D$ of the TfR was specific for the HFE protein, we added an equivalent amount of a soluble version of a classical MHC class I protein, purified H-2K$^d$ complexed with human $\beta$2m (Fahnestock, M. L. et al., *Science* 258:1658-1662 (1992)) to the assay. Addition of this protein had no effect on transferrin binding to the TfR (FIG. 3C) demonstrating that the effect is not solely due to the presence of human $\beta_2$m alone. These experiments independently demonstrate that HFE can effectively lower the affinity of TfR for transferrin and that this effect appears to be a specific property of HFE.

The availability of soluble HFE/$\beta_2$m heterodimers permitted an investigation for other possible ligands for HFE, in particular small peptides which are known to bind class I molecules. The soluble HFE/$\beta_2$m heterodimers were expressed in CHO cells and analyzed for the presence of endogenous peptides by comparing amino acids recovered in acid eluates from HFE with those from other MHC-like proteins which either do or do not bind peptides (UL18 protein (Fahnestock, M. L., et al. *Immunity* 3:583-590 (1995)) and rat FcRn protein (Raghavah, M. et al., *Biochemistry* 32:8654-8660 (1993)), respectively). There was no evidence that peptides were bound to the HFE protein (See Table 1 and Methods). N-terminal protein sequencing demonstrated that no associating proteins were present with the exception of $\beta_2$m (see Methods). Hence, our study has identified only one significant associated polypeptide, the transferrin receptor.

The primary defects in hereditary hemochromatosis appear to be increased iron absorption in the small intestine as well as increased iron deposition in major organs. We have demonstrated that HFE forms a stable complex with the transferrin receptor with the consequence of repressing transferrin uptake. The C282Y mutation is capable of eliminating this interaction. Without being limited to any one theory, these data suggest a mechanism for iron deposition in HFE where a loss of HFE transferrin uptake-repressor function would result in increased cellular uptake of iron. However, the role of this mechanism in intestinal iron absorption is less clear. Recent immunohistochemical studies have localized HFE to the intracellular portion of the cells in the deep crypts of the duodenum (Parkkila, S., et al. *Proc. Natl. Acad. Sci. USA* 94:2534-2539 (1997)), the same region where previous studies have localized the TfR (Banerjee, D. B. et al., *Gastroenterology* 91:861-869 (1986); Anderson, G. J. et al., *Gastroenterolosy* 98:576-585 (1990)). The role of the TfR in the cells of the deep crypts has long been thought to be limited to servicing the proliferative needs of these cells. In light of the association of HFE and the TfR, one must now reconsider the role of transferrin and its receptor in intestinal iron absorption. Regardless of the actual mechanism, the observations described here provide the first molecular link between HFE and iron metabolism. Furthermore, these results demonstrate that by administering HFE protein in situ the amount of transferrin taken up by cells can be attenuated, thereby offering a therapeutic alternative to iron-chelators utilized in iron-overload syndromes of either primary or secondary nature.

In addition, an analysis of the naturally occurring H63D HFE mutation (H41D of the mature protein) was carried out to determine its effect on the affinity of the transferrin receptor for transferrin. The purified H63D-HFE/$\beta_2$m heterodimers were then added to HeLa cells grown in culture and the binding and uptake of $^{125}$I-transferrin measured ("HeLa cell based assay"). It was observed that H63D-HFE/$\beta_2$m heterodimers were 30-40% less efficient in their ability to decrease the transferrin receptor's ("TfR") affinity for transferrin when compared to normal, i.e., wild-type, HFE. At the concentration of 250 nM H63D HFE/$\beta_2$m heterodimers, the TfR had a $K_D$ for transferrin of 28 nM. At the same concentration of normal HFE/$\beta_2$m heterodimers, the TfR had a $K_D$ for transferrin of 40 nM. In the absence of any HFE/$\beta_2$m heterodimers, the TfR had a $K_D$ for transferrin of 7 nM. These data are in agreement with results obtained from experiments in which the H63D mutant protein was overexpressed in 293 cells.

The $K_D$ of the H63D-HFE/$\beta_2$m heterodimers was determined as approximately 105 nM, which is a 50% increase over that observed with the normal HFE/$\beta_2$m heterodimers in the same experiment. These data suggest that the H63D mutation decreases the ability of HFE to alter TfR affinity for transferrin. Therefore, in the presence of the H63D mutation, HFE binds the TfR without decreasing cellular iron uptake to the same degree as the wild-type HFE protein. Therefore, this mutant protein is useful in increasing intracellular concentrations of iron. This soluble protein is expected to bind the TfR on the cell surface and, at an appropriate concentration, out-compete the normal (wild-type) HFE protein for the formation of the HFE/TfR complex. The result would be that the TfR would increase uptake of iron-associated tranferrin into the cell.

A soluble form of the H111A/H145A mutant was purified. The H111A/H145A-HFE/$\beta_2$m heterodimer was tested, using the HeLa cell based assay, for its ability to alter the affinity of TfR for transferrin. At neutral pH and in the presence of 250 nM H111A/H145A-HFE/$\beta_2$m heterodimers, the TfR bound transferrin with a $K_D$ of 12 nM, whereas in the presence of 250 nM wild-type HFE/$\beta_2$m heterodimers the TfR bound transferrin with a $K_D$ of 54 nM. In the absence of any form of HFE, TfR bound transferrin with a $K_D$ of 5 nM. These data also indicate that the H111A/H145A mutant form of HFE, like the H63D mutation, supra, can be useful to increase intracellular iron concentrations by competitively inhibiting the wild-type HFE protein for binding to TfR. Thus, the H111A/H145A mutant of HFE protein may be useful to treat iron deficiency diseases and conditions, like, for example, anemia.

All references (including books, articles, papers, patents, and patent applications) cited herein are hereby expressly incorporated by reference in their entirety for all purposes.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A method for reducing binding of transferrin to a transferrin receptor comprising contacting a transferrin receptor with a soluble complex comprising a $\beta_2$ microglobulin polypeptide and a polypeptide that comprises the amino acid sequence of SEQ ID NO:1.

* * * * *